United States Patent
Akazawa et al.

(10) Patent No.: US 7,094,421 B2
(45) Date of Patent: Aug. 22, 2006

(54) PLASTER CONTAINING 4-BIPHENYLACETIC ACID

(75) Inventors: Mitsuji Akazawa, Ohkawa-gun (JP); Katsuyuki Inoo, Itano-gun (JP); Masahiro Yamaji, Ohkawa-gun (JP)

(73) Assignee: Teikoku Seiyaki Co., Ltd., Kagawa (JP)

( * ) Notice: Subject to any disclaimer, the term of this patent is extended or adjusted under 35 U.S.C. 154(b) by 227 days.

(21) Appl. No.: 10/048,402

(22) PCT Filed: May 31, 2001

(86) PCT No.: PCT/JP01/04583

§ 371 (c)(1),
(2), (4) Date: Jan. 30, 2002

(87) PCT Pub. No.: WO01/91743

PCT Pub. Date: Dec. 6, 2001

(65) Prior Publication Data

US 2002/0173736 A1    Nov. 21, 2002

(30) Foreign Application Priority Data

Jun. 1, 2000    (JP)    ............... 2000-164496

(51) Int. Cl.
*A61F 13/00*    (2006.01)
*A61L 15/16*    (2006.01)
*A61K 9/14*    (2006.01)

(52) U.S. Cl. .................. 424/443; 424/448; 424/449; 424/486

(58) Field of Classification Search ........... 424/448, 424/449, 443, 486; 514/969
See application file for complete search history.

(56) References Cited

U.S. PATENT DOCUMENTS

| 5,262,165 A | * | 11/1993 | Govil et al. ............... 424/448 |
| 5,719,197 A | * | 2/1998 | Kanios et al. ........... 514/772.6 |
| 5,869,087 A | * | 2/1999 | Hirano et al. ............. 424/449 |

FOREIGN PATENT DOCUMENTS

| EP | 0 436 217 A2 | | 7/1991 |
| EP | 0 968 712 A1 | | 1/2000 |
| JP | 03-193728 | | 8/1991 |
| JP | 04-321624 | | 11/1992 |
| JP | 04321624 A | * | 11/1992 |
| JP | 10-218793 | | 8/1998 |
| JP | 10-316560 | | 12/1998 |
| JP | 04312162 A | * | 11/1999 |
| WO | 98/24423 | | 6/1998 |

* cited by examiner

*Primary Examiner*—Michael G. Hartley
*Assistant Examiner*—Micah-Paul Young
(74) *Attorney, Agent, or Firm*—Crowell & Moring LLP

(57) ABSTRACT

It is provided the plaster of anti-inflammatory and analgesic, improving the sustained releasing of 4-biphenylacetic acid from the base adhesive material and low skin irritation, by using more than two kinds of resolvent for 4-biphenylacetic acid having low solubility in solvents. More specifically, it is provided plasters essentially containing 5–50% by weight of styrene-isoprene-styrene block copolymer, 0.05–20% by weight of N-methyl-2-pyrrolidone, 0.1–20% by weight of polyethylene glycol and 0.1–20% by weight of 4-biphenylacetic acid.

23 Claims, 1 Drawing Sheet

1
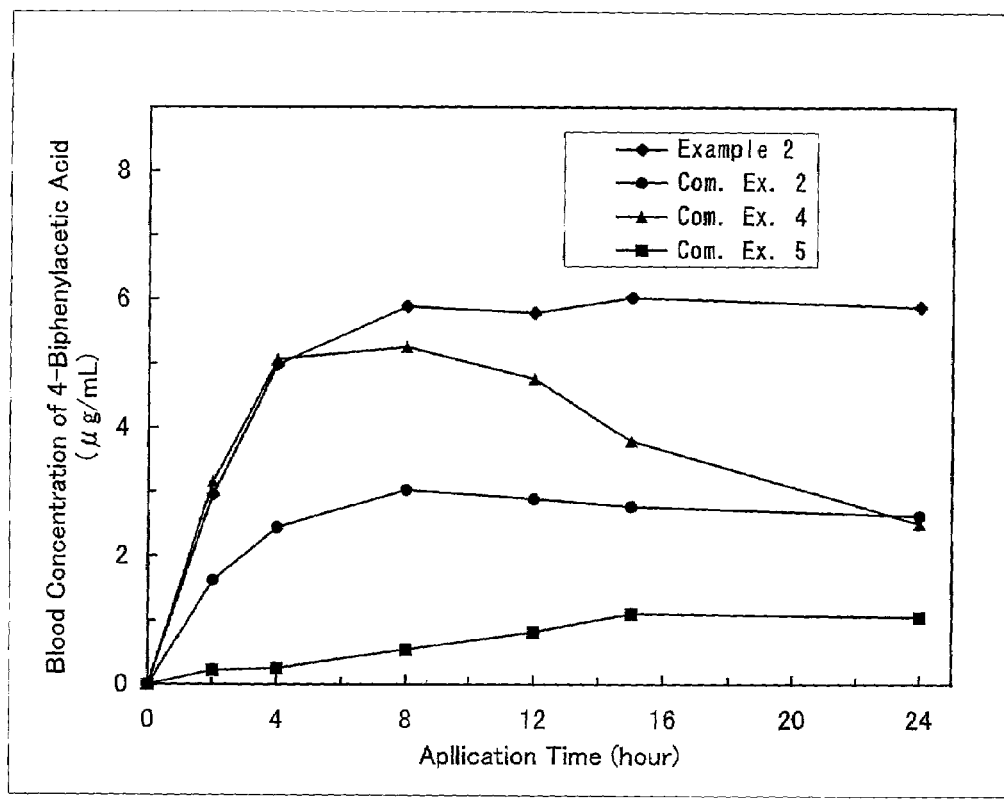

PLASTER CONTAINING 4-BIPHENYLACETIC ACID

TECHNICAL FIELD

The present invention relates to plasters containing styrene-isoprene-styrene block copolymer, N-methyl-2-pyrrolidone, polyethylene glycol and 4-biphenylacetic acid as essential components in an adhesive base material, used as anti-inflammatory drugs and analgesics.

BACKGROUND ART

For administration method of 4-biphenylacetic acid which is non-steroidal anti-inflammatory and analgesic agent, the gel preparation was developed to avoid the systemic side effects thereof and has been used clinically from early stage. However there are some disadvantages that the gel preparation soils the clothes at the time of administration, the gel preparation has to be administered frequently and furthermore the dosage of gel preparation is not regularized. Therefore, the cataplasm contains 4-biphenylacetic acid has developed (Japanese Patent Application Laid-Open No. 193728/1991), and has been marketed.

This developed cataplasm is the preparation that is nearly satisfactory in adhesive power and with the sustained effect of the active ingredient; however, further improvement is desired about continuous adhesive power and sustained effect of the active ingredient. Nevertheless, as for cataplasm, there is a problem in the limitation of the adhesive power and so on, and therefore, to solve these problems, plaster used oily tape as the base material is proposed (Japanese Patent Application Laid-Open No. 321624/1992).

In the plaster proposed in the above, crotamiton is used as a solvent for 4-biphenylacetic acid; however, the solubility of 4-biphenylacetic acid in crotamiton is about 7%, and using small amount of the solvent is insufficient for dissolving of 4-biphenylacetic acid. Furthermore, the crystallization of 4-biphenylacetic acid in the kneaded base material is recognized, and as the result, absorbability and sustained effect of the active ingredient are decreased. On the other hand, in the case of large amount of crotamiton is used for the solvent, there are some problems such as remaining of the base material on the skin by decrease of the adhesive power of the base material, and occurrence of skin irritation.

The inventors of the present invention had made intensive studies to overcome the above-mentioned problems, and succeeded to discover the present invention. That is, the present inventors found out that the plasters containing 4-biphenylacetic acid as an active ingredient in the adhesive base material essentially composed of styrene-isoprene-styrene block copolymer, N-methyl-2-pyrrolidone and polyethylene glycol possess excellent properties to solve such problems at a stroke.

Therefore, the purpose of the present invention is to provide the plasters containing 4-biphenylacetic acid as active ingredient having low degree of skin irritation and high safety margin, in which releasing of 4-biphenylacetic acid from the adhesive base material and sustaining pharmaceutical effect of the active ingredient are improved in comparison with conventional plasters.

DISCLOSURE OF THE INVENTION

One aspect of the present invention is to provide the plasters containing 5–50% by weight of styrene-isoprene-styrene block copolymer, 0.05–20% by weight of N-methyl-2-pyrrolidone, 0.1–20% by weight of polyethylene glycol and 0.1–20% by weight of 4-biphenylacetic acid as essential components.

The specific embodiment of the present invention is to provide the plasters that the combination weight ratio of N-methyl-2-pyrrolidone and polyethylene glycol is in the range of from 1:0.1 to 1:5.

In a more preferred embodiment, the present invention provides the plasters using polyethylene glycol having liquid to semi-solid state at the normal temperature.

Accordingly, in the plasters of the present invention, it is characterized by using the mixture solution of N-methyl-2-pyrrolidone and polyethylene glycol, which is never been examined heretofore, as the resolvent for 4-biphenylacetic acid having slight solubility, and by using styrene-isoprene-styrene block copolymer as the adhesive base material. By having these characteristic points, 4-biphenylacetic acid can be dissolved in the adhesive base material, and the stable releasing of 4-biphenylacetic acid from the base material over the long period of time can be obtained.

As the result of the investigations of the present inventors, the solubility of 4-biphenylacetic acid in the base material is very excellent when N-methyl-2-pyrrolidone is used alone as the resolvent; however, fast releasing 4-biphenylacetic acid from the base material immediately after the administration, that is so-called burst releasing phenomenon, occurred, and therefore, it is difficult to obtain the sustained release of 4-biphenylacetic acid from the plasters.

On the other hand, the solubility of 4-biphenylacetic acid in the base material is not enough in the case of using polyethylene glycol alone as the resolvent and the crystallization of 4-biphenylacetic acid is occurred, and therefore, the releasing of 4-biphenylacetic acid from the base material is insufficient.

Therefore, by combining use of N-methyl-2-pyrrolidone and polyethylene glycol as the resolvent for 4-biphenylacetic acid, 4-biphenylacetic acid can be dissolved completely in the adhesive base material and the fast releasing of 4-biphenylacetic acid just after the administration of the plasters can be controlled.

Furthermore, the degree of skin irritation of the mixture solution of N-methyl-2-pyrrolidone and polyethylene glycol as the resolvent for 4-biphenylacetic acid is extremely low, and therefore, the plasters of the present invention have the excellent high safety margin with extremely low skin irritation.

BRIEF DESCRIPTION OF THE DRAWINGS

FIG. 1 shows the results of Test 3, that is, the measurement of blood concentration using rat on the plasters of the present invention.

BEST MODE FOR CARRING OUT THE INVENTION

The amount of styrene-isoprene-styrene block copolymer in the plasters of the present invention may be 5–50% by weight, more preferably 10–40% by weight. When the amount of styrene-isoprene-styrene block copolymer is less than 5% by weight, aggregated strength of the adhesive base material cannot be achieved and the adhesive base material remains on the skin at the time of release. On the contrary, when the amount of styrene-isoprene-styrene block copolymer is more than 50% by weight, aggregated strength of the adhesive base material is high and decreasing the adhesive power may occur or kneading operation efficiency may decrease.

On the other hand, the amount of N-methyl-2-pyrrolidone as the resolvent may be 0.05–20% by weight, more preferably 0.1–10% by weight. When the amount of N-methyl-2-pyrrolidone is less than 0.05% by weight, it dose not function as the resolvent, and in the case of more than 20% by weight, aggregated strength of the adhesive base material decreases.

Polyethylene glycol to be used for the present invention may be polyethylene glycol having liquid state or semi-solid state at the normal temperature. Such a polyethylene glycol may be polyethylene glycol 200, polyethylene glycol 400, polyethylene glycol 1000, polyethylene glycol 1500 and the like.

The amount of polyethylene glycol may be 0.1–20% by weight, more preferably 1–10% by weight. When the amount of polyethylene glycol is less than 0.1% by weight, the sustained releasing of 4-biphenyladetic acid from the base adhesive material is not recognized. On the contrary, when the amount of polyethylene glycol is more than 20% by weight, the compatibility of polyethylene glycol with the base material becomes insufficient.

The combination weight ratio of N-methyl-2-pyrrolidone and polyethylene glycol is from 1:0.1 to 1:5, more preferably from 1:0.5 to 1:3. When the combination ratio of polyethylene glycol to N-methyl-2-pyrrolidone is less than 0.1, the solubility of 4-biphenylacetic acid to N-methyl-2-pyrrolidone increases and extremely fast release of 4-biphenylacetic acid from the base material occurs and sustained releasing of 4-biphenylacetic acid cannot be obtained. On the contrary, when the combination ratio of polyethylene glycol to N-methyl-2-pyrrolidone is more than 5, it is difficult to obtain high release of 4-biphenylacetic acid from the base material.

On the other hand, the amount of 4-biphenylacetic acid may be 0.1–20% by weight, more preferably 0.5–10% by weight. When the amount of 4-biphenylacetic acid is less than 0.1% by weight, sufficient effect of the active ingredient cannot be obtained. Also, when the amount of 4-biphenylacetic acid is more than 10% by weigh, no more increasing of the desired pharmaceutical effect of the active ingredient is achieved, and therefore, it becomes the wasting of the active ingredient.

In the plasters of the present invention, it is possible to further contain other formulation ingredients, which are used in the conventional plasters. These are, for example, softener such as liquid paraffin, lanolin and the like, tackifier such as alicyclic saturated hydrocarbon resin (e.g., Arkon: Arakawa Chemical Industries, Co.), terpene resin (e.g., YS Resin: Yasuhara Resin Co.), hydrogenated rosin glycerin ester (e.g., Ester Gum: Arakawa Chemical Industries, Co.) and the like, antioxidant such as dibutylhydroxytoluene and the like, filler such as titanium oxide, silicon dioxide and the like, and stimulant such as 1-menthol, peppermint oil, nonylic acid vanillylamide, capsaicin, and the like.

The backing used in the present plasters may not be limited especially, and is preferably the one with no absorption of softener, resolvent, etc. Therefore, the backing of the plasters of the present invention is preferred to be flexible or non-flexible woven or non-woven fabrics and plastic films.

The liner used in the present plasters is polyethylene terephthalate film, polypropylene film and paper etc. The liner is preferably coated with silicon to optimize the peeling properties, if necessarily.

The plasters of the present invention may be manufactured as follows. Namely, styrene-isoprene-styrene block copolymer, softener and tackifier, antioxidant and filler are mixed and dissolved under heating at 150–200° C. in an agitator, and to this mixture is added mixture solution of 4-biphenylacetic acid, N-methyl-2-pyrrolidone and polyethylene glycol, and the resulting mixture is well stirred to obtain homogeneous adhesive material. In this case, the addition of the mixture solution of 4-biphenylacetic acid, N-methyl-2-pyrrolidone and polyethylene glycol is preferably performed under the temperature range of 80–120° C.

Following the above procedure, the resulting adhesive material is spread on the liner with the weight of 50–300 g/m$^2$, and then, laminated with the backing. Then, the backing thus obtained is cut into desired size to produce the plaster of the present invention.

EXAMPLES

The present invention will be further illustrated by the following examples. It is to be understood that the present invention is not limited to these examples. Details may be deleted, added, or substituted as it is deemed to be appropriate, so long as the pharmacological activities of the plaster of the present invention is not changed. Such changes are also covered within the technical scope of the present invention.

Furthermore, the "part" in the following examples means the "part by weight" unless it is specified.

Examples 1 to 4

According to the method for manufacturing the plasters described above, the plasters of the present invention were obtained by the following components.

Example 1

| Components: | |
|---|---|
| styrene-isoprene-styrene block copolymer (Trade name: CARIFLEX TR-1107) | 50.0 part |
| N-methyl-2-pyrrolidone | 0.5 part |
| polyethylene glycol 400 | 0.5 part |
| 4-biphenylacetic acid | 0.5 part |
| butylhydroxytoluene | 2.0 part |
| liquid paraffin | 46.5 part |
| Total | 100.0 part |

Example 2

| Components: | |
|---|---|
| styrene-isoprene-styrene block copolymer (Trade name: CARIFLEX TR-1111) | 15.0 part |
| N-methyl-2-pyrrolidone | 5.0 part |
| polyethylene glycol 400 | 5.0 part |
| 4-biphenylacetic acid | 5.0 part |
| butylhydroxytoluene | 2.0 part |
| liquid paraffin | 21.5 part |
| polybutene | 15.0 part |
| tackifier (rosin ester) | 30.0 part |

Example 3

| Components: | |
|---|---|
| styrene-isoprene-styrene block copolymer (Trade name: CARIFLEX TR-1111) | 10.0 part |
| N-methyl-2-pyrrolidone | 15.0 part |
| polyethylene glycol 400 | 10.0 part |
| 4-biphenylacetic acid | 8.0 part |
| butylhydroxytoluene | 2.0 part |
| liquid paraffin | 25.0 part |
| tackifier (alicyclic saturated hydrocarbon resin) | 30.0 part |
| Total | 100.0 part |

Example 4

| Components: | |
|---|---|
| styrene-isoprene-styrene block copolymer (Trade name: CARIFLEX TR-1111) | 25.0 part |
| N-methyl-2-pyrrolidone | 3.0 part |
| polyethylene glycol 20000 | 5.0 part |
| 4-biphenylacetic acid | 4.0 part |
| butylhydroxytoluene | 2.0 part |
| liquid paraffin | 31.0 part |
| tackifier (rosin ester) | 30.0 part |
| Total | 100.0 part |

Comparative Example 1

| Components: | |
|---|---|
| styrene-isoprene-styrene block copolymer (Trade name: CARIFLEX TR-1107) | 50.0 part |
| liquid paraffin | 46.0 part |
| butylhydroxytoluene | 2.0 part |
| crotamiton | 1.0 part |
| 4-biphenylacetic acid | 1.0 part |
| Total | 100.0 part |

The prescribed amount of styrene-isoprene-styrene block copolymer, softener and antioxidant were mixed and the resulting mixture was stirred for 60 minutes at 110–200° C. under the nitrogen gas atmosphere to obtain the dissolved substance. Then, to the dissolved substance was added the mixture of the active ingredient and crotamiton, and the mixture was further stirred for 20 minutes to obtain the homogeneous material. Subsequently, the homogenous material was spread on the backing with the optional thickness, and laminated with the liner. Then, the backing thus obtained was cut into desired size to obtain the plaster of the Comparative Example 1.

Comparative Example 2

| Components: | |
|---|---|
| styrene-isoprene-styrene block copolymer (Trade name: CARIFLEX TR-1107) | 26.0 part |
| liquid paraffin | 49.5 part |
| butylhydroxytoluene | 2.0 part |
| tackifier (rosin ester) (Trade name: KE-311) | 15.0 part |
| crotamiton | 2.5 part |
| 4-biphenylacetic acid | 5.0 part |
| Total | 100.0 part |

The prescribed amount of styrene-isoprene-styrene block copolymer, softener, tackifier and antioxidant were mixed and the resulting mixture was stirred for 60 minutes at 110–200° C. under the nitrogen gas atmosphere to obtain the dissolved substance. Then, to the dissolved substance was added the mixture of the active ingredient and crotamiton, and the mixture was further stirred for 20 minutes to obtain the homogeneous material. Subsequently, the homogenous material was spread on the backing with the optional thickness, and laminated with the liner. Then, the backing thus obtained was cut into desired size to obtain the plaster of the Comparative Example 2.

Comparative Example 3

| Components: | |
|---|---|
| styrene-isoprene-styrene block copolymer (Trade name: CARIFLEX TR-1107) | 25.0 part |
| liquid paraffin | 52.0 part |
| butylhydroxytoluene | 2.0 part |
| tackifier (rosin ester) (Trade name: KE-311) | 5.0 part |
| crotamiton | 15.0 part |
| 4-biphenylacetic acid | 1.0 part |
| Total | 100.0 part |

According to the above-mentioned components, the plaster of the Comparative Example 3 was obtained in accordance with the same manufacturing method described in the Comparative Example 2.

Comparative Example 4

| Components: | |
|---|---|
| styrene-isoprene-styrene block copolymer (Trade name: CARIFLEX TR-1111) | 15.0 part |
| butylhydroxytoluene | 2.0 part |
| liquid paraffin | 28.0 part |
| tackifier (rosin ester) | 30.0 part |
| polybutene | 15.0 part |

-continued

| Components: | |
|---|---|
| light anhydrous silicic acid | 1.0 part |
| 1-menthol | 0.5 part |
| Total | 100.0 part |

-continued

| Components: | |
|---|---|
| N-methyl-2-pyrolidone | 5.0 part |
| 4-biphenylacetic acid | 5.0 part |
| Total | 100.0 part |

Styrene-isoprene-styrene block copolymer, softener, tackifier, antioxidant were dissolved in the agitator under 150–200° C., and to this mixture was added the mixture of 4-biphenylacetic acid and N-methyl-2-pyrolidone to obtain the homogeneous material. In this case, the addition of the mixture of 4-biphenylacetic acid and N-methyl-2-pyrrolidone was conducted under the temperature range of 80–120° C. Then, the plaster of Comparative Example 4 was obtained from the resulting homogeneous material by the conventional methods.

Comparative Example 5

| Components: | |
|---|---|
| styrene-isoprene-styrene block copolymer (Trade name: CARIFLEX TR-1111) | 15.0 part |
| butylhydroxytoluene | 2.0 part |
| liquid paraffin | 23.0 part |
| tackifier (rosin ester) | 30.0 part |
| polybutene | 15.0 part |
| polyethylene glycol 400 | 10.0 part |
| 4-biphenylacetic acid | 5.0 part |
| Total | 100.0 part |

According to the above-mentioned components, the plaster of the Comparative Example 5 was obtained in accordance with the same manufacturing method described in the Comparative Example 4. In this Comparative Example 5, polyethylene glycol was used as the resolvent instead of N-methyl-2-pyrrolidone in the Comparative Example 4.

The skin irritation test, observation of crystallization appearance in the adhesive base material, and drug releasing test of the plasters of the present invention were conducted comparison to the plasters obtained in Comparative Examples. These results were described below.

Test 1: Skin Primary Irritation Test on Rabbits

Nine (9) Japanese white rabbits (female) were used as one test group. The back region of rabbit was shaved, and four portions in the shaved region (2 portions each of the right and left sides) were used as the application portions. The right 2 portions were used as healthy portions, and the left 2 portions were used as damaged portions. For the damaged portions, skin of rabbit was damaged with cutting # pattern by using the needle. Each plaster (having 2.5 cm×2.5 cm in size: produced in Examples 1 and 2, and Comparative Example 3) was applied on the skin. The applied plasters were fixed with adhesive tapes and further covered with protectors in order to avoid the movement of plasters.

The plasters were taken out after 24 hours, and the skin irritation reaction were observed at the point of 1, 24, 48 and 72 hours after the removal of the plasters.

Evaluation of the skin irritation reaction was made in accordance with the criterion of Draize method listed in the following Table 1, and the skin primary irritation index (P.I.I.) were calculated from the scores obtained at 1 and 48 hours after the removal of the plasters.

The safety of each plaster was evaluated by using the categories of safety evaluation listed in Table 2, and presented in Table 3 below.

TABLE 1

The Criterion of Draize Method
Observation items and the degree

| Erythema and Eschar formation | No change | 0 |
|---|---|---|
| | Very slight erythema (Barely perceptible) | 1 |
| | Well defined erythema | 2 |
| | Moderate to strong erythema | 3 |
| | Severe erythema with slight eschar formation (with injuries extended to depth) | 4 |
| Edema formation | No change | 0 |
| | Very slight edema (Barely perceptible) | 1 |
| | Slight edema (Having clear contour of edema) | 2 |
| | Moderate edema (Swollen about 1 mm height) | 3 |
| | Severe edema (Swollen more than 1 mm height and expanded to other area) | 4 |

TABLE 2

The Categories of Safety Evaluation

| P.I.I. | Category of Safety |
|---|---|
| P.I.I. = 0 | No irritant |
| 0 < P.I.I. < 2 | Slight irritant |
| 2 ≦ P.I.I. < 5 | Moderate irritant |
| 5 ≦ P.I.I. | Strong irritant |

TABLE 3

| Tested plasters | Skin condition | Erythema 1 hr | Erythema 48 hr | Edema 1 hr | Edema 48 hr | P.I.I. | Category of Safety Evaluation |
|---|---|---|---|---|---|---|---|
| Example 1 | Healthy | 0.2 | 0.0 | 0.0 | 0.0 | 0.2 | Slight irritant |
| | Damaged | 0.3 | 0.2 | 0.0 | 0.0 | | |
| Example 2 | Healthy | 0.8 | 0.2 | 0.0 | 0.0 | 0.6 | Slight irritant |
| | Damaged | 0.8 | 0.5 | 0.0 | 0.0 | | |
| Compara. Example 3 | Healthy | 2.7 | 1.7 | 0.2 | 0.0 | 2.8 | Moderate irritant |
| | Damaged | 3.2 | 2.5 | 0.7 | 0.3 | | |

As apparent from the results of Table 3, the plasters of the present invention had no skin irritation to be problems.

Test 2: Observation of Crystallization Appearance

The adhesive base material of each plaster was spread thinly on the prepared slide and the appearance of 4-biphenylacetic acid in the adhesive base material was observed with the polarizing microscope (Nikon OPTIPHOTO 02-POL).

The result is presented in Table 4 below.

TABLE 4

| Tested Plasters | Presence of crystalline |
|---|---|
| Example 2 | Non |
| Example 4 | Non |
| Comparative Example 1 | Existence |
| Comparative Example 2 | Existence |
| Comparative Example 5 | Existence |

As is clear from the result, there was no crystallization of 4-biphenylacetic acid occurring in the plasters of the present invention.

Test 3: Blood Concentration Measurement Test on Rats

The back region of Wistar rats (male, 5–6 weeks old) was shaved, and 5 rats having no abnormal skin were used as one test group for this test.

The each plaster (having 2×3 cm in size: produced in Example 2, and Comparative Examples 2, 4 and 5) was applied on the skin. The blood samples were taken out at 0, 2, 8 and 24 hours after applying the plasters, and the amount of 4-biphenylacetic acid were measured by high performance liquid chromatography (HPLC).

The results were shown in the FIG. 1.

As apparent from the results shown in the FIG. 1, the plasters of the present invention released active ingredient from the adhesive base material in high concentration continuously and for long period of time.

From the above-mentioned results, it is confirmed that the releasing of the active ingredient and the sustaining of the pharmaceutical effect of the active ingredient of the present invention are improved in comparison with the conventional plasters, as well as the degree of skin irritation is decreased, and therefore the plasters of the present invention have high safety margin.

INDUCTRIAL APPLICABILITY

As mentioned above, due to the using of N-methyl-2-pyrolidone and polyethylene glycol used as the resolvent for 4-biphenylacetic acid in the plasters of the present invention, the releasing of the active ingredient from the adhesive base material and the sustaining of the pharmaceutical effect of the active ingredient are improved in comparison with the conventional plasters, as well as the degree of skin irritation is decreased, and therefore, the plasters of the present invention have high safety margin.

The invention claimed is:

1. A plaster comprising 5–50% by weight of styrene-isoprene-styrene block copolymer, 0.05–20% by weight of N-methyl-2-pyrrolidone, 0.1–20% by weight of polyethylene glycol, and 0.1–20% by weight of 4-biphenylacetic acid, wherein the ratio of N-methyl-2-pyrrolidone to polyethylene glycol is in the range of 1:0.1–1:5.

2. A plaster according to claim 1, wherein the polyethylene glycol is liquid or semi-solid at room temperature.

3. A plaster according to claim 1, comprising 10–40% by weight of styrene-isoprene-styrene block copolymer, 0.1–10% by weight of N-methyl-2-pyrrolidone, 1–10% by weight of polyethylene glycol and 0.5–10% by weight of 4-biphenylacetic acid.

4. A plaster according to claim 1, further comprising at least one member selected from the group consisting of softeners, tackifiers, antioxidants, fillers, and stimulants.

5. A plaster according to claim 4, wherein said softener is liquid paraffin or lanolin.

6. A plaster according to claim 4, wherein said tackifier is an alicyclic saturated hydrocarbon resin, a terpene resin, or a hydrogenated rosin glycerin ester.

7. A plaster according to claim 4, wherein said antioxidant is butyihydroxytoluene.

8. A plaster according to claim 4, wherein said filler is titanium oxide or silicon dioxide.

9. A plaster according to claim 4, wherein said stimulant is l-menthol, peppermint oil, nonylic acid vanillylamide or capsalcin.

10. A plaster according to claim 2, wherein said polyethylene glycol (PEG) is selected from the group consisting of PEG 200, PEG 400, PEG 1000, and PEG 1500.

11. A plaster according to claim 1, wherein said ratio of N-methyl-2-pyrrolidone to polyethylene glycol is in the range of 1:0.5–1:3.

12. A plaster according to claim 1, further comprising a backing.

13. A plaster according to claim 12, wherein said backing is a flexible or non-flexible woven or non-woven fabric or a plastic film.

14. A plaster according to claim 12, further comprising a liner.

15. A plaster according to claim 14, wherein said liner is polyethylene terephthalate or polypropylene film or paper.

16. A plaster according to claim 15, wherein said liner is coated with silicon.

17. A plaster consisting essentially of 5–50% by weight of styrene-isoprene-styrene block copolymer, 0.05–20% by weight of N-methyl-2-pyrrolidone, 0.1–20% by weight of polyethylene glycol, and 0.1–20% by weight of 4-biphenylacetic acid.

18. A plaster according to claim 17, further including at least one member selected from the group consisting of softeners, tackifiers, antioxidants, fillers, and stimulants.

19. A method of making a plaster as defined in claim 1, comprising:

(A) mixing and dissolving styrene-isoprene-styrene block copolymer and optionally a member of the group consisting of softener, a tackifier, an antioxidant, a filler, and mixtures thereof;

(B) adding a mixture of 4-biphenylacetic acid, N-methyl-2-pyrrolidone, and polyethylene glycol, to form a coating mixture; and (C) spreading said coating mixture on a substrate.

20. A method of making a plaster according to claim 19, wherein said coating mixture is spread on said substrate at a weight of 50–300 g of coating per $m^2$.

21. A method of making a plaster according to claim 20, wherein said substrate is a liner, further comprising laminating said liner bearing said coating with a backing.

22. A method of making a plaster according to claim 20, wherein said substrate is a backing, further comprising laminating said backing bearing said coating with a liner.

23. A method of administering 4-biphenylacetic acid to a patient comprising topically applying a plaster according to claim 1 to the skin of the patient.

* * * * *